United States Patent [19]

Pearson

[11] Patent Number: 5,116,574

[45] Date of Patent: * May 26, 1992

[54] CONTINUOUS TREATMENT PROCESS AND APPARATUS FOR THE DISINFECTION OF INFECTIOUS WASTE

[76] Inventor: Erich H. Pearson, 925 Oakwood Ct., Glen Ellyn, Ill. 60137

[*] Notice: The portion of the term of this patent subsequent to Dec. 31, 2008 has been disclaimed.

[21] Appl. No.: 679,601

[22] Filed: Apr. 3, 1991

[51] Int. Cl.$^5$ ............................................. G05B 13/00
[52] U.S. Cl. ...................................... 422/3; 210/173; 210/195.3; 210/252; 210/295; 210/513; 210/760; 241/DIG. 38; 241/152.1; 422/28; 422/32; 422/38; 422/140; 422/145; 422/186.07; 422/231; 422/234
[58] Field of Search ................... 402/3, 26, 29, 32, 38, 402/139-140, 145, 186.07, 224, 231, 234; 241/152 R, 152 A, DIG. 38, 21, 24, 29; 210/173, 195.3, 252, 295, 513, 760, 764

[56] References Cited

U.S. PATENT DOCUMENTS

| | | | |
|---|---|---|---|
| 2,246,224 | 6/1941 | Streander | 210/173 |
| 3,547,577 | 12/1970 | Lovercheck | 53/511 |
| 3,549,528 | 12/1970 | Armstrong | 422/28 X |
| 3,772,188 | 11/1973 | Edwards | 210/15 |
| 3,772,999 | 11/1973 | Miller et al. | 34/57 A |
| 3,790,091 | 2/1974 | Law et al. | 241/24 |
| 3,817,458 | 6/1974 | Gilberto | 241/20 |
| 3,876,157 | 4/1975 | McIntire et al. | 241/17 |
| 3,897,330 | 7/1975 | Rhys | 209/75 |
| 3,926,379 | 12/1975 | Dryden et al. | 241/69 |
| 4,066,024 | 1/1978 | O'Connor | 110/8 F |
| 4,133,638 | 1/1979 | Healey | 422/32 |
| 4,145,007 | 3/1979 | Jetzer | 241/24 |
| 4,160,722 | 7/1979 | Marsh | 209/4 |
| 4,178,239 | 12/1979 | Lowther | 210/15 |
| 4,194,968 | 3/1980 | Pfalzer et al. | 209/3 |
| 4,234,560 | 11/1980 | Kuerten et al. | 422/224 X |
| 4,313,827 | 2/1982 | Ratigan et al. | 210/136 |
| 4,391,413 | 7/1983 | Pack | 241/99 |
| 4,578,185 | 3/1986 | Wilson et al. | 210/85 |
| 4,618,103 | 10/1986 | Wilson et al. | 241/41 |
| 4,619,409 | 10/1986 | Harper et al. | 241/38 |
| 4,846,964 | 7/1989 | Scott et al. | 208/428 |
| 4,884,756 | 12/1989 | Pearson | 241/42 |
| 5,077,007 | 12/1991 | Pearson | 422/3 |
| 5,078,965 | 1/1992 | Pearson | 422/3 |

OTHER PUBLICATIONS

Undated advertisement from Ozone Research & Equipment Corporation, entitled "Typical Ozone Applications".

Undated advertisement entitled "Patented Ozonair Wastewater Treatment System".

Primary Examiner—Robert J. Warden
Assistant Examiner—Amalia L. Santiago
Attorney, Agent, or Firm—Roper & Quigg

[57] ABSTRACT

A process and apparatus for continuously treating infectious waste, which comprises: (a) introducing bulk unseparated infectious waste material into a receiving container, the receiving container adapted to receive a flow of disinfectant such that the receiving container remains substantially free of infectious contaminants; (b) shredding the waste material by a primary shredder; (c) separating the shredded waste material from waste residue in a separation tank having a predetermined fluid level thereby producing a waste slurry; (d) pumping the waste slurry into a reactor vessel; (e) contacting the waste slurry with a disinfecting fluid in the reactor vessel for a sufficient amount of time to disinfect the waste slurry; and (f) dewatering the disinfected waste slurry to recover solid disinfected waste material.

28 Claims, 1 Drawing Sheet

CONTINUOUS TREATMENT PROCESS AND APPARATUS FOR THE DISINFECTION OF INFECTIOUS WASTE

BACKGROUND OF THE INVENTION

1. Field of the Invention

The invention relates to a process and apparatus for the treatment of infectious waste in a rapid, cost efficient manner, with materially less environmental impact than the historically practiced art. More particularly, the invention relates to an apparatus and method for the continuous treatment of biologically contaminated medical waste, such as syringes, gowns, bedding, containers, bandages and other liquid or solid materials which may be contaminated with infectious bacterial and viral agents, or with organic contaminants such as chemopharmaceuticals, oxidizable solvents, and the like, in a reactor utilizing gas oxidation. The process and apparatus can also be used to recover recyclable materials obtained from the incoming waste stream.

2. Description of the Prior Art

The disposition of infectious waste is an issue which has received considerable attention among governmental environmental agencies and the public and within the waste disposal industry. Inappropriate disposal practices, as evidenced by infectious medical waste washing up on the beaches of oceans and lakes, as well as being found in ordinary trash containers in public areas, supports the concern that currently practiced treatment and disposal methods are inadequate to handle, in a safe, cost effective manner, the volume of infectious waste being generated today. A process to treat economically large volumes of infectious medical waste in an environmentally acceptable fashion not heretofore used to treat such waste, is therefore needed.

Historically, most infectious waste has been treated by incineration, with the incineration residue thereafter being landfilled or dumped in the oceans. However, recent studies performed on emissions generated from the combustion of medical waste, even from facilities equipped with advanced air pollution control equipment, have demonstrated consistent emission of priority metals, acid gases, and carcinogenic organics such as 2, 3, 7, 8 furans and dioxin. (United States Environmental Protection Agency, *Hospital Waste Combustion Study*, December, 1988). It is the potential toxicity of emissions from medical waste incineration which has driven the capital and operating cost of incineration and pollution control equipment beyond the reach of most hospitals needing to replace old, inefficient, uncontrolled units. Controversy relating to incinerator emissions has also resulted in substantial public opposition to the construction of private or commercial incineration facilities. The consequence has been that demand for the treatment of medical waste has exceeded available supply, and commercial incinerators have, in instances, overcharged the generators of medical waste. This creates an even greater potential for illicit disposal.

Another method traditionally used for decontamination involves steam sterilization in autoclaves. However, autoclaves are not appropriate for economically treating large volumes of infectious waste, and have questionable effectiveness on certain microorganisms. Further, autoclaves do not change the inherent visual appearance of waste, resulting in uncertainty and fear among those persons responsible for its subsequent handling. Many cases have been reported of autoclaved waste being rejected at landfills.

Others have attempted liquid chemical disinfection of medical waste. For instance, U.S. Pat. No. 3,926,379 teaches a continuous process for the decontamination of solid items of comparatively small size, such as hypodermic syringes. This material is introduced through a feed tube to a hammermill, along with a disinfectant liquid delivered by pump. Pulverized solid waste then drops to a bag or drawer. Disinfectant drains from the bag and is reused. However, with this device, the potential for microbial aerosols exists, as well as the inability to assure that the disinfectant solution has not become neutralized and therefore inactive. Finally, the device is limited to solid, friable objects of small size; it is not suitable for bulk, loose wastes as received from hospitals.

U.S. Pat. No. 4,618,103 discloses a continuous process wherein solid medical waste is treated with disinfectant fluid during and after introduction to a high speed hammermill. Waste is manually introduced through a rotatable door along with disinfectant solution. Waste drops to a settling/separation tank, from which disinfectant solution is discharged continuously to a sewer, and solid residue is removed manually. As in U.S. Pat. No. 3,926,379, this method appears intended for small, solid objects in limited quantity; it is therefore not suitable for large volumes of medical waste.

U.S. Pat. No. 4,619,409 teaches a continuous process wherein solid medical waste is treated with disinfectant fluid during and after introduction to a high speed hammermill. Waste material is continuously conveyed to a second conveyor which operates an automatic door ahead of the hammermill. Milled waste drops to a settling/separation tank, from which disinfectant solution is discharged continuously to a sewer, and solid residue is removed manually. As in the previous patents cited above, this method utilizes a high speed hammermill to achieve particle size reduction. Hammermills are suitable when applied to friable materials, but in practice have not proven efficient or effective in achieving particle size reduction with non-friable materials, such as sheet plastic or woven synthetics, neither of which can easily be fractured at standard conditions. Sheet plastics and woven materials comprise a substantial percentage of contaminated medical waste. Further, the method disclosed by this patent is not readily suitable for tonnage quantities of medical waste, owing to the need for manual removal of milled waste from the settling tank, thereby placing humans in contact with the material. Also, as in the previous patents cited above, there is no ability to assure the effectiveness of decontamination on a continuous basis, and none of these patents provide, by themselves, an efficient method of generating treated, recyclable by-products. Finally, as in the previous patents cited, there does not exist the ability to treat other liquid organic wastes typically found among medical waste, for instance chemopharmaceutical materials or solvents, prior to discharge to a municipal sewer.

Applicant's prior U.S. Pat. No. 4,884,756 discloses an apparatus for the treatment of medical waste on a continuous process basis. However, applicant's prior apparatus is not suitable for gas oxidation using a reactor vessel for the disinfecting of medical wastes, nor is there the ability for improved quality control of the treatment process with applicant's prior apparatus as there is with the continuous treatment process of the instant invention. Finally, this prior patent cannot separate the waste stream by component to produce suitably recyclable materials.

Applicant has overcome the above-discussed shortcomings of the prior art by providing a continuous process for separating and disinfecting infectious waste, such as infectious medical waste. The process generally comprises:

(a) introducing bulk unseparated infectious waste material into a receiving container means, said receiving container means adapted for receiving a flow of disinfectant such that said receiving container means remains substantially free of infectious contaminants;

(b) shredding the waste material by a primary shredding means;

(c) separating components of the shredded waste material in a separation tank means having a predetermined fluid level thereby producing at least one waste slurry stream;

(d) transferring the waste slurry stream into a reactor vessel means;

(e) contacting the waste slurry stream with a disinfecting fluid in the reactor vessel means for a sufficient amount of time to disinfect the waste slurry stream; and (f) dewatering the disinfected waste slurry stream to recover solid disinfected waste material.

In addition, the process of the present invention optionally provides additional shredding means located downstream from the separation tank means for further shredding the waste materials in the waste slurry stream, as necessary. The disinfectant preferably comprises ozone in gas phase and/or in aqueous solution.

As noted, other shredding means, such as for example secondary and tertiary shredding means, may be employed if necessary to further reduce the size of particles in the waste slurry stream prior to pumping the same into the reactor vessel means. All of the shredder means utilized in the process of the invention are preferably low speed, high torque rotary shredders. The secondary and tertiary shredders, if employed, are preferably adapted for in-line submerged applications, because these shredders are disposed below the fluid level of the separation tank means.

The waste slurry stream (comprising from about 1% to about 10% by weight shredded solids) is pumped for a sufficient amount of time to allow the waste slurry stream to fill the reactor vessel means to a predetermined level.

Ozone gas, in a concentration of from about 0.5% to about 10% by weight, is preferably employed as the disinfecting fluid in the reactor vessel means. In order to maximize contact with the ozone gas, the waste slurry stream may be flowed through a gas contactor, associated with the reactor vessel, in a direction opposite to the buoyancy of ozone gas bubbles in the contactor, although co-current or cross-current flows are equally useful if the residence time and turbulence of the waste slurry in the contactor means is adjusted accordingly. For example, when using counter-current flow, the waste slurry is flowed through the contactor at a rate which preferably exceeds the buoyant velocity of the ozone gas bubbles. Ozone gas bubbles having an average diameter of about 1 millimeter are preferably utilized.

The disinfection process is preferably monitored continuously by an analyzing means associated with the reactor vessel means, to assure that sufficient disinfecting fluid is introduced into and maintained in the reactor vessel means. Contacting times from about 5 to about 45 minutes have been found to be sufficient to effectively disinfect typical infectious waste materials.

The present invention also contemplates an apparatus for the treatment of infectious waste. The apparatus comprises:

(a) a receiving container means for receiving bulk infectious waste material, said receiving container means being adapted to receive a flow of disinfectant from a disinfectant means for disinfecting the surfaces of said receiving container means;

(b) a primary shredding means in association with the receiving container means, for reducing the particle size of the infectious waste material;

(c) a separation tank means connected to the primary shredding means, for separating components of the shredded waste material and forming a waste slurry stream, the separation tank means having a fluid filling means for filling the tank means to a predetermined level;

(d) a reactor vessel means for disinfecting the waste slurry stream, the reactor vessel means comprising:

(i) at least two reactor vessels, the first of which is disposed in a position to receive the waste slurry stream from the separation tank means and the remainder of which disposed to communicate in series relationship, with such series commencing with the first reactor vessel, each such reactor vessel having associated therewith a gas contactor;

(ii) a disinfecting fluid generating means connected with each of the contactors, for continuously introducing a disinfecting fluid into the contactor and the reactor vessel means;

(iii) a recirculation port means associated with each of the at least two reactor vessels, for flowing the waste slurry stream through each of the at least two reactor vessels; and (iv) an analyzing means associated with the reactor vessel means, for continuously monitoring the amount of disinfecting fluid introduced by the disinfecting fluid generating means and the amount of disinfecting fluid utilized in the reactor vessel means; and (e) dewatering means associated with the reactor vessel means, for recovering solid, disinfecting waste material from the disinfected waste slurry.

The apparatus may include secondary and tertiary shredding means, as described above, if needed to provide a waste slurry stream having a further reduced particle size.

The reactor vessel means which forms an essential part of the subject apparatus generally comprises from about 1 to about 10 reactor vessel units connected in series The number of vessels employed will depend on a number of factors described in detail below. Each reactor vessel includes a gas contactor, which may extend longitudinally from the top of the reactor vessel toward the bottom thereof, where the contactor is in connecting relation with the recirculation port means.

The disinfecting fluid generating means used to disinfect infectious waste according to the present invention preferably comprises an ozone generator. The ozone gas disinfecting fluid may be generated from either compressed air or high purity oxygen.

BRIEF DESCRIPTION OF THE DRAWING

For a more complete understanding of this invention, reference should be made to the drawing, as briefly described below.

DESCRIPTION OF THE PREFERRED EMBODIMENTS

Figure 1:
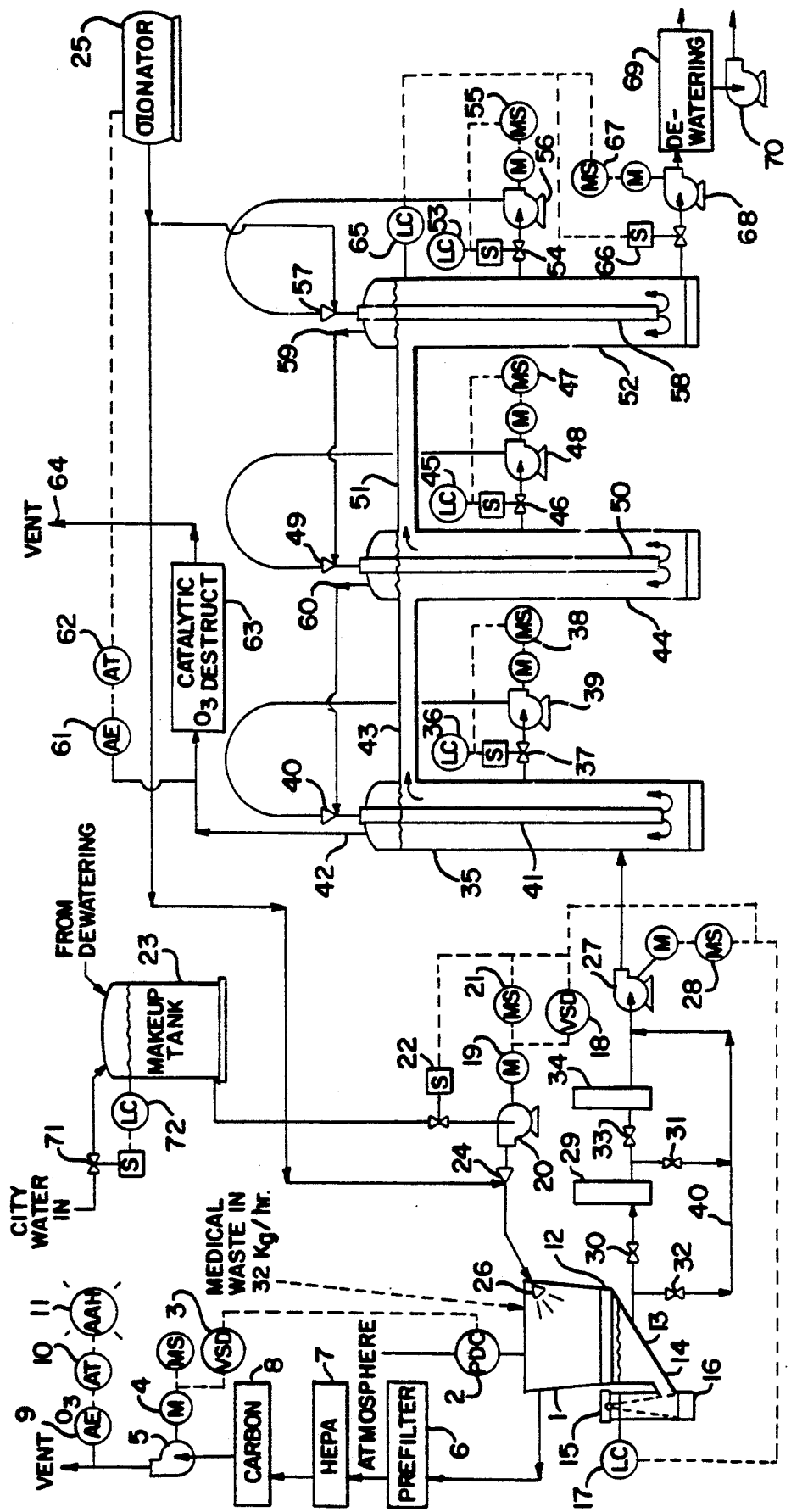
FIG. 1 is a schematic representation of the particle size reduction and reactor vessel apparatus and continuous process utilizing gas oxidation for the treatment of infectious waste according to the present invention.

Referring in detail to FIG. 1, there is illustrated a particle size reduction apparatus and process used to reduce the particle size of infectious waste material, which waste material will subsequently be disinfected using the reactor vessel apparatus and ozone gas oxidation process also shown in detail in FIG. 1.

Referring to FIG. 1, bulk infectious medical waste (not shown) is introduced to receiving hopper 1. Air pressure within hopper 1 is maintained negative relative to ambient air pressure by pressure differential controller 2. This controller transmits an electrical signal to variable speed drive 3, which modulates the speed of motor 4 driving ventilation fan 5. Alternatively, a manual or automatically actuated mechanical damper may be used to regulate the volume of air drawn by ventilation fan 5. The speed of ventilation fan 5 is sufficient to maintain a flow of air into hopper 1 at a velocity adequate to minimize the escape of microbial aerosols and odors from the hopper infeed opening. Of course, the exact air velocity is dependent on the nature of the waste materials, the size of the infeed opening to the hopper 1, and other factors as will be appreciated by one skilled in the art.

Air induced from hopper 1 by ventilation fan 5 is drawn through prefilter 6, HEPA (High Efficiency Particulate Arresting) filter 7, and activated carbon filter 8, prior to release to the atmosphere. These filters assure that the exhausted air is substantially free of contaminated aerosols, odors, and trace ozone.

Ozone not adsorbed onto carbon filter 8 is detected by analysis element 9, which transmits an electrical signal to analysis transmitter 10, energizing alarm 11. Alarm 11 signals any condition in which ozone, as detected by analysis element 9, exceeds one-half the Short Term Exposure Limit for ozone (STEL), or 0.15 ppm, as established by ACGIH (1989).

Bulk infectious waste within hopper may be fed by gravity, or other conveyor methods (not shown), from hopper 1 to primary shredder 12. Primary shredder 12 is preferably a low speed, high torque rotary shear shredder, which is suitable for coarsely shredding high concentrations of nonfriable materials commonly found in medical waste, such as sheet plastic and woven or synthetic materials. Primary shredder 12 is designed with sufficient torque to shred metallic objects which also could be found in medical waste.

Coarsely shredded waste material from primary shredder 12, which may have particle sizes of about 4 cm or smaller, discharges vertically downward to separation tank 13. In separation tank 13, the shredded waste materials are saturated with a predetermined amount of water through a line (not shown) from tank 23 to form a slurry containing from about 1% to about 10%, and preferably about 5%, suspended solids by weight. Heavier glass and metallic objects settle to the sloped base of separation tank 13, and then continue to settle through transition 14 to settling tank 15. The separation of such larger objects is beneficial so that these objects do not damage or inhibit the operation of subsequent treatment stages. Lifting basket 16, located at the bottom of settling tank 15 and below the level of transition 14, may be manually removed through the top of settling tank 15 to evacuate the settled materials.

Alternatively, separation tank 13 may include commercially available apparatus for repulping and separating the paper fiber component of the incoming waste material. In this case, the paper pulp would be withdrawn from separation tank 13 and treated as described hereinafter. Nonfibrous components, such as for example glass and metal can be separated as described above and treated as set forth below. The separation of such waste material into various components would thus facilitate the recycling and reuse of the separated components subsequent to treatment.

Slurry level within separation tank 13 is maintained at a predetermined level by level controller 17. Level controller 17 transmits an electrical signal to variable speed drive 18, which modulates the speed of motor 19 driving makeup pump 20. The out flow of makeup pump 20 and eductor 24 may be valved to direct water to the separation tank 13, with the valve (not shown) actuated in response to a signal from the level controller 17. Alternatively, level controller 17 may transmit an electrical signal to energize motor starter 21 and the coil for solenoid valve 22.

Makeup pump 20 draws water from makeup tank 23 and forces this water through eductor 24. Eductors are commercially available devices which are suitable for providing efficient mass transfer between two compressible fluids. Eductors are venturi-type devices which include an inlet convergent section, typically conical, a venturi orifice of a diameter generally about 25% of the diameter of the inlet, and a gradually divergent section after the venturi orifice. The accelerated velocity of a fluid passing through the venturi orifice decreases the pressure of the fluid per Bernoulli's law; this low pressure may then be employed to induce and mix secondary fluids. Release from the venturi orifice to the divergent section of the eductor results in high turbulence and, thus, efficient mixing of the two fluids. In the process of the present invention, eductors have been found to achieve mass transfer rates of ozone gas into water of up to 99%; however, other commercially available means for achieving ozone mass transfer may also be employed, including bubble columns and in-line static mixers, as one skilled in the art will appreciate.

Ozone gas, generated by ozonator 25, is induced into and mixed with water within eductor 24. This ozonated water is then sprayed through nozzle 26 into receiving hopper 1 at a rate, regulated by level controller 17, sufficient to maintain a predetermined slurry level within separation tank 13. Nozzle 26 is designed and located to continuously expose the interior surfaces of hopper 1 to ozonated makeup water from makeup pump 20. Ozonated water has a high disinfecting efficacy, and thus maintains an aseptic environment within hopper 1. Any ozone still in gas phase (e.g., undissolved in water from eductor 24) functions to neutralize odor and microbial aerosols within hopper 1.

Alternatively, the ozonated water from make-up pump 20 can be fed continuously or intermittently to the nozzle 26, with the outflow from eductor 24 also being directed via a line (not shown) to the separation tank means 13 to maintain a predetermined fluid level within the tank means 13 wherein the waste slurry is formed.

If desired, other disinfecting agents may be employed in conjunction with, or in lieu of, the ozone gas disinfectant. Examples of such additional disinfecting agents include alkali metal perborate salts such as sodium perborate monohydrate or sodium perborate anhydrous; alkali metal hypochlorite salts such as sodium perborate anhydrous; alkali metal hypochlorite salts such as sodium hypochlorite; peroxide salts such as calcium peroxide, urea hydrogen peroxide or hydrogen peroxide; chlorine; chlorinated lime; oxychlorosene; and mixtures of these agents.

Other suitable disinfecting agents which may be used in accordance with the invention include essential oils such as thymol or eucalyptol; phenol; sodium phenolate; triclosan; hexachlorophene; hexedidine; hexedine; sanguinarine; quaternary ammonium compounds such as cetylpyridinium chloride, benzethonium chloride or benzalkonium chloride; chlorhexidine; octenidine; alexidine; ambazone; povidoneiodine; quinolines such as benzoxiquine, broxyquinoline, chloroxine, chlorquinaldol, 8-hydroxyquinoline or 8-hydroxyquinoline sulfate; cupric sulfate; and mixtures thereof.

The disinfecting agents listed above may be employed in amounts effective to achieve the desired disinfecting results. This amount will vary depending upon the particular disinfecting agent(s) employed, the nature of the infectious waste treated, and the disinfecting strength and toxicity of the particular disinfecting agent(s), in accordance with principles well-known in the art.

Once the waste slurry reaches a predetermined level in separation tank 13, separated slurry is induced from separation tank 13 by transfer pump 27, which is started by an electrical signal from level controller 17 to motor starter 28.

Efficient particle size reduction of the waste material is necessary to provide maximum surface area for exposure to the disinfectant in the subsequent disinfecting stage shown in FIG. 1. If no additional particle size reduction is required subsequent to the primary stage, as determined by the quality of waste to be treated, secondary and tertiary shredding stages may be bypassed by closing valve 30, opening valve 32 and directing the flow of the waste slurry to pump 27 via line 90. If secondary shredding in shredder 29 is required, to produce a smaller particle size, such as for example to about 20 mm, valves 32 and 33 are closed, and valves 30 and 31 opened; the slurry exiting secondary shredder 29 is then directed to the pump 27 via line 90. If tertiary shredding in shredder 34 is also required, to further reduce the shredded particle size, such as for example to about 5 mm, valves 32 and 31 are closed and valves 30 and 33 are opened.

Secondary shredder 29 and tertiary shredder 34 are, like primary shredder 12, low speed, high torque rotary shear shredders, which have proven to be the most effective means of achieving size reduction of nonfriable materials. However, secondary shredder 29 and tertiary shredder 34 are designed specifically for in-line, submerged applications. Tertiary shredder 34 is identical to secondary shredder 29 except for the width of the rotary cutter knives, as cutter width determines final shredded product size.

Although not depicted in FIG. 1, secondary and tertiary shredders 29 and 34 may be arranged in parallel trains, i.e., there may be two secondary and two tertiary shredders. The use of parallel trains may have operational advantages. In this regard, the present invention is not deemed limited to the single train configuration shown in FIG. 1.

Referring again in detail to FIG. 1, there is illustrated the preferred embodiment of the inventive continuous treatment apparatus and process utilizing gas oxidation in a reactor vessel apparatus and process.

As shown in detail in FIG. 1, shredded waste slurry from the shredding apparatus and process is pumped, via transfer pump 27 through at least one reactor vessel, and preferably a series of reactor vessels, each designed to achieve a percent reduction of resident microorganisms. The actual number of treatment stages is determined by: (1) the quantity of microorganisms in the untreated waste, as measured by population or concentration in standardized units, such as Colony Forming Unit per milliliter (CFU/ml); (2) the quality of microorganisms in the untreated waste, as measured by the known resistance to neutralization by chemical oxidation for the specific species in question; (3) the degree of disinfection desired; (4) the presence of chemical interferences in the waste slurry, such as organic constituents which consume ozone at variable rates, which could individually or in the aggregate reduce the quantity of ozone available to neutralize microorganisms in any given treatment stage; and (5) the presence of mechanical interferences, such as incomplete mixing, or the availability of fine adsorbent particles providing large adsorbing surface areas, which tend to shield microorganisms from exposure to disinfectants.

Treated slurry may technically be safe for subsequent handling without achieving a 100% reduction during the treatment process; however, one skilled in the art will appreciate that additional treatment stages may be employed to achieve sterility, if that is the desired objective.

According to one preferred aspect of the invention (shown in FIG. 1), three reactor vessels are connected in series to form the disinfecting stage of the invention. As previously described, from 1 to about 10 reactor vessels may be employed as the reactor vessel means. These reactor vessels are sealed from the external environment, but permit the flow of slurry between individual vessels, as described below. Modeling studies indicate that six passes through a gas contactor, and a total retention time of about 5 to about 45 minutes, preferably on the order of about 30 minutes, is sufficient to achieve decontamination under most conditions.

In order to initiate the disinfecting stage of the inventive process, transfer pump 27 directs the waste slurry to reactor vessel 35. Reactor vessel 35 has a diameter which is about 20 percent of the side water depth. Other tank geometries known to those of ordinary skill in the art are possible to the extent that they do not produce regions of stagnant flow. Reactor vessel 35 is filled to a predetermined level regulated by level controller 36 at which point an electrical signal is transmitted to the actuator for valve 37, and to motor starter 38, which starts recirculation pump 39.

Pump 39 directs slurry from reactor vessel 35 through mixer 40. The mixer 40 (as well as the mixers 49 and 57) may be an eductor or an in-line static mixer known in the art, or a mix of such. In potential large scale commercial applications, the slurry may be flowed through mixer 40 at a rate of about 1460 kg/min. and a pressure of 4.2 kg/cm$^2$, in order to maintain a slurry velocity of about 49 meters/second across the eductor venturi orifice of the mixer 40. These specifications are applicable for an eductor-type mixer 40 having an orifice diameter of 2.5 cm, which is about the smallest orifice diameter which would reliably pass typical slurried waste containing solid particles up to a diameter of about 12 mm. Larger eductors may readily be used at correspondingly higher flow rates and smaller eductors may be used at correspondingly lower flow rates, with the principal point being that the size of the eductor orifice must pass the largest particles in the slurry so that clogging is avoided. The principles of operation for mixer 40 are identical to those for eductor 24, described above. Eductors are suitable for use as mixing devices in the present invention because they do not employ static or dynamic elements which could collect solids and eventually obstruct flow. However, as noted above, other types of in-line high shear mixers, emulsifiers, and homogenizers may also be employed, depending on the actual composition of the waste slurry.

Mixer 40 discharges vertically downward through reactor tube 41, located along the axis of reactor vessel 35. Reactor tube 41 may also be located exterior to vessel 35, provided that its discharge into vessel 35 does not create undesirable vortices. Slurry velocity within reactor tube 41 is about 1.1 meters/second, or any velocity sufficiently greater than the buoyant velocity of ozone gas bubbles (about 0.3 meters/second).

The efficient mixing of mixer 40, the presence of ozone gas bubbles averaging about 1 mm diameter (which maximizes surface area per unit mass of ozone gas), the flow of slurry within reactor tube 41 counter to the buoyancy of ozone gas bubbles, and the approximate 4 second slurry retention time within the reactor tube all combine to provide intimate liquid/gas mixing, mass transfer, and efficient decontamination.

Slurry is discharged at the bottom of reactor tube 41 in a region above the base of reactor vessel 35. Ozone gas bubbles coalesce as they rise to the surface of the slurry with the vessel 35 and are evacuated through vent 42. However, reactor vessel 35 may also be designed without freeboard (the airspace above the slurry level), by relocating duct 43 to the top of reactor vessel 35. In this way, flow through reactor vessel 35 would be more nearly laminar. In this case, ozone gas could be released in an auxiliary vessel (not shown) located between reactor vessel 35 and subsequent treatment stages.

Transfer pump 27 continues to fill reactor vessel 35 to the level of duct 43. The slight pressure differential between reactor vessel 35 and duct 43 results in the flow of slurry from reactor vessel 35 to reactor vessel 44.

When the slurry reaches a predetermined level in reactor vessel 44, level controller 45 transmits an electrical signal to the actuator for valve 46, and to motor starter 47, to start recirculation pump 48. Pump 48 directs slurry through mixer 49 and reactor tube 50 in the same manner as delineated above for reactor vessel 35. Duct 51, located at an elevation substantially equivalent to duct 43, then transfers slurry to reactor vessel 52. When the slurry reaches a predetermined level in vessel 52, level controller 53 transmits an electrical signal to the actuator for valve 54, and to motor starter 55, which starts recirculation pump 56. Pump 56 directs slurry through mixer 57 and reactor tube 58 in the same manner as described for reactor vessel 35.

Ozone gas is generated from ozonator 25 at a rate of about 70 grams $O_3$ per minute and at a concentration of about 0.5% to about 10% by weight, preferably about 2% by weight (if generated from compressed air), or about 5% by weight (if generated from high purity oxygen).

It will be understood that using lower concentrations of ozone will increase the contact time required to destroy bacterial and viral microorganisms, and using higher concentrations of ozone will reduce the necessary contact time. Also, the additional disinfecting agents described above may be used in place of, or in conjunction with, the preferred ozone disinfectant.

The ozone gas disinfecting fluid is introduced to the series of reactor vessels counter to the flow of slurry: ozone is first induced by mixer 57 and used in reactor vessel 52. Offgas from vessel 52 is evacuated through vent 59 and is induced by mixer 49, to be used in reactor vessel 44. Offgas from vessel 44 is evacuated through vent 60 and induced by mixer 40, to be used in reactor vessel 35. Offgas from vessel 35 is relieved through vent 42.

Analysis element 61 continuously measures the ozone concentration in the offgas from reactor vessel 35, and analysis transmitter 62 regulates the rate of ozone production from ozonator 25 by electrical signals so that an excess of ozone is maintained in the offgas from reactor vessel 35. An excess of ozone at this point assures that sufficient ozone is available for decontamination throughout the system, and that ozone is employed with maximum efficiency.

If desired, ozone may also be introduced to reactor vessels 35, 44 and 52 in parallel rather than in series, e.g., from a common manifold serving mixers 40, 49, and 57, respectively. Offgas would then also be directed to common or discrete offgas treatment. However, the introduction of ozone in parallel may not result in as high a utilization efficiency.

After being analyzed for ozone concentration, offgas from reactor vessel 35 is directed through ozone destruct unit 63, which may consist of any of several commercially available $O_3$ decomposition systems employing heat and catalysts to decompose ozone to oxygen at an efficiency of at least 99%. After treatment, gases may be exhausted through vent 64.

Reactor vessel 52 continues to fill to the elevation of duct 51. At this point, level controller 65 transmits an electrical signal to the actuator for valve 66, and to motor starter 67, to start discharge pump 68. Pump 68 transfers slurry from reactor vessel 52, at a rate equivalent to the inlet rate for transfer pump 27, to dewatering system 69.

Dewatering system 69 may be any of several commercially available liquid/solid separation devices, including, but not limited to centrifuges, belt filters, vacuum filters, filter presses, gravity filters, extruders, flash driers, radiant driers, etc., depending on the final retained moisture content desired. Liquid filtrate from dewatering system 69 is transferred by recycle pump 70 to makeup tank 23. Fresh makeup water is then added to makeup tank 23 through valve 71, the actuator for which is signalled by level controller 72, as needed to maintain a predetermined makeup water level within tank 23.

After dewatering, solid decontaminated waste material is recovered from the dewatering device. The solid decontaminated waste material is suitable for nonhazardous waste landfill, or if appropriate, may be recycled.

The following examples are given to illustrate the invention, but are not deemed to be limiting thereof. All percentages given throughout the specification are based on weight, 100% weight basis, unless otherwise indicated.

EXAMPLES 1-14

The following examples are based on modeling studies designed to simulate the reactor vessel series of the invention. The quantity of infectious waste slurry treated and the percent of suspended solids by weight (TSS) is indicated in the table corresponding to each example. Solids treated consisted of approximately 49% paper and paper products, 49% molded plastics and woven synthetics, and 1% each of glass and metal, the percentages being by weight. This composition is similar to that for infectious medical waste. Inoculum consisted of 250 ml nutrient broth containing the following bacteria species: *Bacillus subtilis, Staphylococcus aureus, Pseudomonas aeruginosa,* and *Eschericha coli.* The diluted initial concentration of inoculum is indicated as the plate count for the first run of each example (at 0 minutes elapsed time).

Slurry was pumped from the reactor vessel through an ozone contactor, and returned to the vessel. Slurry samples were drawn from a ¾" gate valve located on the pressure side of the pump, with samples placed into 125 ml sterile specimen containers for incubation and plate count analysis by an independent, certified microbiological testing laboratory. Process flow was measured by an ultrasonic, non-intrusive flowmeter. With process flow and elapsed time as measured variables, the number of passes through the ozone contactor at each sampling interval was calculated, as indicated in the tables below.

Ozone was introduced using compressed ambient air as a parent gas for Examples 1-6, and for Example 14. Ozone was introduced using high purity oxygen as a parent gas for Examples 7-13. Ozone concentration by weight ranged from 0.8% to 1.8% for tests using compressed air as a feed gas, and from 2% to 4% using oxygen as a feed gas. Results indicated that the quantity of ozone required to achieve the desired bacterial reduction was somewhat higher when oxygen was used as a feed gas, with ozone generated at higher concentrations.

For Examples 6-11, slurry was deliberately contaminated with known concentrations of organic materials to measure the effect of organic interferences. Although significant, bacterial reduction was not achieved to the desired level for Examples 10 and 11. However, for these tests the slurry was deliberately contaminated with organics (solvents) to a concentration of 1500 ppm by weight, resulting in a COD (chemical oxygen demand) of 8000 mg/l for Example 10 and 7000 mg/l for Example 11. Bacterial reduction was also significant for Example 14, although incomplete. However, during this test frequent plugging of the pump and sample port was experienced, and cross contamination was suspected.

The results of the examples are set forth in Tables 1-14 below. As indicated therein, six passes through an ozone contactor and a net retention time of thirty minutes, provided effective neutralization of microorganisms in the treated waste materials.

TABLE 1

Example 1
Tank Slurry, kg: 118
TSS, %: 1.5
Parent Gas: COMPRESSED AIR
Organics Added, ppm NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.476 | 0.0 | 130000 | 0.0000 | 0.00 |
| Run 2 | 0.82 | 1.495 | 0.5 | 350000 | −169.2308 | 0.48 |
| Run 3 | 1.35 | 0.961 | 1.0 | 3000000 | −2207.6923 | 0.93 |
| Run 4 | 1.63 | 0.961 | 1.5 | 700000 | −438.4615 | 1.34 |
| Run 5 | 2.97 | 0.856 | 3.5 | 0 | 100.0000 | 2.94 |
| Run 6 | 4.13 | 0.587 | 5.5 | 0 | 100.0000 | 4.48 |
| Run 7 | 6.67 | 1.437 | 8.5 | 0 | 100.0000 | 6.28 |
| Run 8 | 10.48 | 1.516 | 12.5 | 0 | 100.0000 | 8.65 |
| Run 9 | 14.41 | 1.392 | 16.5 | 0 | 100.0000 | 10.63 |

TABLE 2

Example 2
Tank Slurry, kg: 118
TSS, %: 1.5
Parent Gas: COMPRESSED AIR
Organics Added, ppmw NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.67 | 0.00 | 2000000 | 0.0000 | 0.00 |
| Run 2 | 2.55 | 1.24 | 2.00 | 1500000 | 25.0000 | 1.40 |
| Run 3 | 5.26 | 1.71 | 4.00 | 50000 | 97.5000 | 2.56 |
| Run 4 | 7.61 | 1.57 | 6.00 | 6000 | 99.7000 | 3.71 |
| Run 5 | 12.51 | 1.64 | 10.00 | 300 | 99.9850 | 6.86 |
| Run 6 | 14.54 | 1.63 | 11.50 | 200 | 99.9900 | 8.01 |
| Run 7 | 15.21 | 1.62 | 12.00 | 6500 | 99.6750 | 8.39 |
| Run 8 | 18.31 | 1.66 | 14.50 | 200 | 99.9900 | 10.36 |
| Run 9 | 21.63 | 1.60 | 17.00 | 300 | 99.9850 | 12.45 |
| Run 10 | 29.17 | 1.65 | 22.00 | 0 | 100.0000 | 17.30 |

TABLE 3

Example 3
Tank Slurry, kg: 113
TSS, %: 2.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.76 | 0.00 | 1500000 | 0.0000 | 0.00 |
| Run 2 | 1.17 | 1.13 | 2.00 | 3000000 | −100.0000 | 1.30 |
| Run 3 | 2.51 | 1.10 | 4.00 | 500 | −99.9667 | 2.60 |
| Run 4 | 4.12 | 1.16 | 6.00 | 150 | −99.9900 | 3.89 |
| Run 5 | 5.67 | 1.11 | 8.00 | 0 | 100.0000 | 5.19 |
| Run 6 | 6.89 | 1.17 | 9.50 | 0 | 100.0000 | 6.17 |
| Run 7 | 9.09 | 1.13 | 12.00 | 0 | 100.0000 | 7.79 |
| Run 8 | 11.38 | 1.17 | 14.50 | 0 | 100.0000 | 9.41 |

TABLE 4

Example 4
Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.00 | 0.00 | 110000 | 0.0000 | 0.00 |
| Run 2 | 0.83 | 1.08 | 1.00 | 110000 | 0.0000 | 0.50 |
| Run 3 | 2.56 | 1.12 | 3.00 | 900000 | −718.1818 | 1.50 |
| Run 4 | 3.70 | 1.17 | 5.00 | 3000 | 97.2727 | 2.49 |
| Run 5 | 4.81 | 1.27 | 7.00 | 100 | 99.9091 | 3.49 |
| Run 6 | 5.89 | 1.38 | 9.00 | 0 | 100.0000 | 4.49 |
| Run 7 | 8.02 | 1.37 | 13.00 | 0 | 100.0000 | 6.49 |

TABLE 5

Example 5
Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.57 | 0.00 | 11000 | 0.0000 | 0.00 |
| Run 2 | 0.40 | 0.93 | 1.00 | 13000 | −18.1818 | 0.50 |
| Run 3 | 0.79 | 0.92 | 2.00 | 3100 | 71.8182 | 1.00 |
| Run 4 | 1.29 | 0.98 | 3.00 | 0 | 100.0000 | 1.50 |
| Run 5 | 1.81 | 1.02 | 4.00 | 0 | 100.0000 | 2.00 |
| Run 6 | 2.29 | 0.97 | 5.00 | 500 | 95.4545 | 2.49 |
| Run 7 | 2.73 | 0.96 | 6.00 | 0 | 100.0000 | 2.99 |
| Run 8 | 3.18 | 1.03 | 7.00 | 130 | 98.8182 | 3.49 |
| Run 9 | 3.63 | 1.07 | 8.00 | 200 | 98.1818 | 3.99 |

TABLE 6

Example 6
Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 0.315 | 0.00 | 550000 | 0.0000 | 0.00 |
| Run 2 | 0.40 | 0.923 | 1.00 | 130000 | 76.3636 | 0.50 |
| Run 3 | 0.84 | 0.852 | 2.00 | 700 | 99.8727 | 1.00 |
| Run 4 | 1.63 | 0.777 | 4.00 | 300 | 99.9455 | 2.00 |
| Run 5 | 2.07 | 0.961 | 5.00 | 0 | 100.0000 | 2.49 |
| Run 6 | 2.47 | 0.845 | 6.00 | 100 | 99.9818 | 2.99 |
| Run 7 | 4.32 | 0.972 | 10.00 | 100 | 99.9818 | 4.99 |
| Run 8 | 5.09 | 0.872 | 12.00 | 0 | 100.0000 | 5.99 |

TABLE 7

Example 7
Tank Slurry, kg: 147
TSS, %: 3.5
Parent Gas: OXYGEN
Organics Added, ppmw: 1000

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 4.78 | 0.00 | 750000 | 0.0000 | 0.00 |
| Run 2 | 1.27 | 3.97 | 1.00 | 25000 | 96.6667 | 0.50 |
| Run 3 | 2.96 | 4.02 | 2.00 | 95000 | 87.3333 | 1.00 |
| Run 4 | 4.57 | 4.04 | 3.00 | 3000 | 99.6000 | 1.50 |
| Run 5 | 7.02 | 3.82 | 4.00 | 350 | 99.9533 | 2.00 |
| Run 6 | 9.38 | 3.81 | 5.00 | 250 | 99.9667 | 2.49 |
| Run 7 | 11.40 | 3.99 | 6.00 | 0 | 100.0000 | 2.99 |

TABLE 8

Example 8
Tank Slurry, kg: 147
TSS, %: 3.5
Parent Gas: OXYGEN
Organics Added, ppmw: 1000

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 5.19 | 0.00 | 170000 | 0.0000 | 0.00 |
| Run 2 | 4.33 | 3.87 | 2.00 | 75000 | 55.8824 | 1.00 |
| Run 3 | 9.27 | 3.87 | 4.00 | 750 | 99.5588 | 2.00 |
| Run 4 | 13.60 | 3.87 | 6.00 | 0 | 100.0000 | 2.99 |
| Run 5 | 14.49 | 4.02 | 7.00 | 330 | 99.8059 | 3.49 |
| Run 6 | 16.89 | 3.95 | 9.00 | 0 | 100.0000 | 4.49 |
| Run 7 | 19.26 | 3.88 | 11.00 | 0 | 100.0000 | 5.49 |
| Run 8 | 21.79 | 4.03 | 13.00 | 0 | 100.0000 | 6.49 |
| Run 9 | 24.94 | 3.82 | 15.00 | 0 | 100.0000 | 7.48 |

TABLE 9

Example 9
Tank Slurry, kg: 147
TSS, %: 3.5
Parent Gas: OXYGEN
Organics Added, ppmw: 1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.33 | 0.00 | 150 | 0.0000 | 0.00 |
| Run 2 | 2.57 | 3.83 | 2.00 | 100 | 33.3333 | 1.00 |
| Run 3 | 5.85 | 3.92 | 4.00 | 0 | 100.0000 | 2.00 |
| Run 4 | 9.01 | 3.77 | 6.00 | 0 | 100.0000 | 2.99 |
| Run 5 | 12.20 | 3.84 | 8.00 | 3000 | −1900.00 | 3.99 |
| Run 6 | 14.69 | 3.82 | 10.00 | 0 | 100.0000 | 4.99 |
| Run 7 | 17.59 | 4.35 | 12.00 | 0 | 100.0000 | 5.99 |
| Run 8 | 20.39 | 3.70 | 14.00 | 0 | 100.0000 | 6.98 |
| Run 9 | 23.11 | 3.68 | 16.00 | 0 | 100.0000 | 7.98 |
| Run 10 | 26.56 | 3.87 | 18.00 | 0 | 100.0000 | 8.98 |
| Run 11 | 29.65 | 3.88 | 20.00 | 0 | 100.0000 | 9.98 |

TABLE 10

Example 10
Tank Slurry, kg: 170
TSS, %: 3.0
Parent Gas: OXYGEN
Organics Added, ppmw: 1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.90 | 0.00 | 3100000 | 0.0000 | 0.00 |
| Run 2 | 2.12 | 4.60 | 1.00 | 14000000 | −351.6129 | 0.43 |
| Run 3 | 4.81 | 3.05 | 3.00 | 11000000 | −254.8387 | 1.29 |
| Run 4 | 7.95 | 3.11 | 5.00 | 5000000 | −61.2903 | 2.16 |
| Run 5 | 11.26 | 3.04 | 7.00 | 700000 | 77.4194 | 3.02 |
| Run 6 | 13.38 | 2.29 | 10.00 | 900000 | 70.9677 | 4.31 |
| Run 7 | 15.02 | 2.55 | 12.00 | 140000 | 95.4839 | 5.18 |
| Run 8 | 16.61 | 2.30 | 14.00 | 7000 | 99.7742 | 6.04 |

TABLE 10-continued

Example 10
Tank Slurry, kg:       170
TSS, %                 3.0
Parent Gas:            OXYGEN
Organics Added, ppmw   1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 9 | 18.40 | 2.52 | 16.00 | 11000 | 99.6452 | 6.90 |

TABLE 11

Example 11
Tank Slurry, kg:       161
TSS, %                 3.0
Parent Gas:            OXYGEN
Organics Added, ppmw   1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.27 | 0.00 | 1500000 | 0.0000 | 0.00 |
| Run 2 | 1.50 | 3.47 | 1.00 | 300000 | 80.0000 | 0.68 |
| Run 3 | 3.42 | 2.34 | 3.00 | 4500 | 99.7000 | 2.05 |
| Run 4 | 5.19 | 1.82 | 5.00 | 4000 | 99.7333 | 3.42 |
| Run 5 | 7.21 | 1.77 | 7.00 | 3900 | 99.7400 | 4.78 |
| Run 6 | 8.57 | 1.72 | 9.00 | 4000 | 99.7333 | 6.16 |
| Run 7 | 9.92 | 1.72 | 11.00 | 1000 | 99.9333 | 7.45 |
| Run 8 | 11.07 | 1.67 | 13.00 | 100000 | 93.3333 | 8.74 |

TABLE 12

Example 12
Tank Slurry, kg:       147
TSS, %                 5.0
Parent Gas:            OXYGEN
Organics Added, ppmw   NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.63 | 0.00 | 50000 | 0.0000 | 0.00 |
| Run 2 | 1.24 | 3.47 | 1.00 | 2000 | 96.0000 | 0.55 |
| Run 3 | 3.62 | 2.67 | 3.00 | 300 | 99.4000 | 1.66 |
| Run 4 | 6.86 | 2.60 | 5.00 | 0 | 100.0000 | 2.76 |
| Run 5 | 10.14 | 2.61 | 7.00 | 0 | 100.0000 | 3.87 |
| Run 6 | 14.48 | 2.73 | 10.00 | 0 | 100.0000 | 5.52 |
| Run 7 | 17.31 | 2.70 | 12.50 | 0 | 100.0000 | 6.91 |
| Run 8 | 21.27 | 2.74 | 15.50 | 0 | 100.0000 | 8.56 |

TABLE 13

Example 13
Tank Slurry, kg:       125
TSS, %                 3.5
Parent Gas:            OXYGEN
Organics Added, ppmw   NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 2.75 | 0.00 | 1000000 | 0.0000 | 0.00 |
| Run 2 | 1.22 | 2.74 | 1.00 | 500000 | 50.0000 | 1.10 |
| Run 3 | 4.29 | 2.48 | 3.00 | 50000 | 95.0000 | 3.30 |
| Run 4 | 6.49 | 2.56 | 5.00 | 100 | 99.9900 | 5.90 |
| Run 5 | 8.44 | 2.41 | 7.00 | 0 | 100.0000 | 8.25 |
| Run 6 | 10.51 | 2.52 | 9.00 | 0 | 100.0000 | 10.48 |

TABLE 14

Example 14
Tank Slurry, kg:       125
TSS, %                 3.5
Parent Gas:            OXYGEN
Organics Added, ppmw   NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.505 | 0.00 | 700000 | 0.0000 | 0.00 |

TABLE 14-continued

Example 14
Tank Slurry, kg: 125
TSS, %  3.5
Parent Gas: OXYGEN
Organics Added, ppmw NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 2 | 0.96 | 1.211 | 2.00 | 700000 | 0.0000 | 1.32 |
| Run 3 | 2.33 | 1.142 | 5.00 | 15000 | 97.8571 | 3.30 |
| Run 4 | 3.64 | 1.173 | 8.00 | 10000 | 98.5714 | 5.28 |
| Run 5 | 4.74 | 1.271 | 11.00 | 9000 | 98.7143 | 7.26 |
| Run 6 | 6.91 | 1.268 | 15.00 | 6500 | 99.0714 | 9.90 |
| Run 7 | 8.39 | 1.412 | 18.00 | 7000 | 99.0000 | 11.88 |
| Run 8 | 9.71 | 1.406 | 21.00 | 7000 | 99.0000 | 13.86 |
| Run 9 | 10.94 | 1.382 | 24.00 | 4000 | 99.4286 | 15.84 |
| Run 10 | 12.80 | 1.296 | 28.00 | 1000 | 99.8571 | 18.48 |

The following Table 15 provides typical waste loading and flow rates for a commercial facility having the capacity of treating approximately 50 tons of medical waste per 24 hour day under the assumptions that the slurry concentration in the separation tank 13 is 5% solids by weight and that the dewatering efficiency is 50%. Such loadings, flow rates and assumptions are merely representative and are not intended to limit the scope of the present invention or the appended claims.

TABLE 15

| | |
|---|---|
| 1. Waste feed to receiving hopper 1, Kg/hr. | 32 |
| 2. Discharge of makeup pump 20, Kg/min. | 604 |
| 3. Fresh water makeup to makeup tank 23, Kg/min. | 29 |
| 4. Water velocity through eductor 24, m/sec. | 27 |
| 5. Differential pressure across eductor 24, Kg/cm$^2$ | 4.2 |
| 6. Air velocity into inlet of receiving hopper 1, m/sec. | 1 |
| 7. Slurry flow through transfer pump 27, Kg/min. | 636 |
| 8. Diameter of reactor vessels 35, 44, 52, m. | 1.2 |
| 9. Side water depth of reactor vessels 35, 44, 52, m. | 5.2 |
| 10. Capacity of reactor vessels 35, 44, 52, Kg. | 6460 |
| 11. Volume of reactor vessels 35, 44, 52, l. | 5880 |
| 12. Retention in each of reactor vessels 35, 44, 52, min. | 10 |
| 13. Slurry flow through pumps 39, 48, 56, Kg/min. | 1460 |
| 14. Differential pressure across mixers 40, 49, 57, Kg/cm$^2$ | 4.2 |
| 15. Inlet diameter of mixers 40, 49, 57, cm. | 10 |
| 16. Orifice diameter of mixers 40, 49, 57, cm. | 2.5 |
| 17. Slurry velocity through mixers 40, 49, 57, m/sec. | 49 |
| 18. Diameter of reactor tubes 41, 50, 58, cm. | 15 |
| 19. Length of reactor tubes 41, 50, 58, m. | 5 |
| 20. Retention time in reactor tubes 41, 50, 58, min. | 4.2 |
| 21. Ozone concentration (air as parent gas), % | 2 |
| 22. Ozone concentration (oxygen as parent gas), % | 5 |
| 23. Ozone production, gm/min. | 70 |
| 24. Gas flow (air as parent gas), Kg/min. | 3.5 |
| 25. Gas flow (oxygen as parent gas), Kg/min. | 1.4 |
| 26. Gas flow pressure, Kg/cm$^2$ | 0.7 |
| 27. Dewatered solids output, Kg/min. | 64 |
| 28. Water recycle, Kg/min. | 572 |

The invention being thus described, it will be apparent that the same may be varied in many ways. Such variations are not to be regarded as a departure from the spirit and scope of the invention and all such modifications are intended to be included within the scope of the claims.

What is claimed is:

1. A process for the continuous treatment of infectious waste material, which comprises:
   (a) introducing bulk unseparated infectious waste material into a receiving container means, said receiving container means being in communication with a shredding means whereby bulk unseparated infectious waste material supplied to said receiving container means is conducted to said shredding means;
   (b) shredding said bulk unseparated waste material by said shredding means;
   (c) transferring the shredded waste material from said shredding means to a separation tank means having a fluid filling means to provide a predetermined fluid level in said separation tank means and removing from said shredded waste material any glass and metal components which settle by gravity in a lowermost portion of said separation tank means to form a waste slurry;
   (d) transferring said waste slurry from said separation tank means of step (c) to a disinfection vessel means, said disinfection vessel means comprising a first disinfection means communicating in series relationship with at least one second disinfection means, and contacting said waste slurry in said disinfection vessel means with a disinfectant comprising ozone in gas phase and in aqueous solution for a sufficient amount of time to disinfect said waste slurry; and
   (e) transferring said disinfected waste slurry to a dewatering means to remove liquid therefrom said recover solid components of said disinfected waste slurry.

2. The process of claim 1, wherein said ozone in gas phase comprises ozone gas diluted in air.

3. The process of claim 1, wherein said ozone in gas phase is present in a concentration of from about 0.5% to about 10% by weight of said disinfectant.

4. The process of claim 1, wherein said waste slurry of step (c) is flowed through a disinfection tube positioned centrally in said disinfection vessel means in a direction opposite to the buoyancy of ozone gas bubbles in contact with said waste slurry.

5. The process of claim 4, wherein said waste slurry is flowed downward through said disinfection tube at a rate of about 1.1 meters per second.

6. The process of claim 4, wherein said ozone gas bubbles are generated with an average diameter of about 1 millimeter.

7. The process of claim 1, wherein the concentration of said ozone is continuously monitored by analyzing means communicating with said disinfection vessel means.

8. The process of claim 1, wherein said second disinfection means comprises from 1 to about 10 disinfection tanks communicating is series relationship.

9. The process of claim 1, further including the step of introducing said disinfectant into said receiving container means to disinfect surfaces of said receiving container means.

10. The process of claim 1, wherein said shredding means comprises a rotary shear shredder, said shredding means communicating with said receiving container means.

11. The process of claim 1, further including the step of transferring said waste slurry from said separation tank means of step (c) to a second shredding means and reducing the size of particles in said waste slurry by said second shredding means prior to transferring said waste slurry into said disinfection vessel means.

12. The process of claim 11, further including the step of transferring said waste slurry from said second shredding means to a third shredding means to further reduce the size of particles in said waste slurry prior to transferring said waste slurry into said disinfection vessel means.

13. The process of claim 11, wherein said second shredding means comprises a rotary shear shredder, said second shredding means being in communication with said separation tank means and disposed below said predetermined fluid level of said separation tank means.

14. The process of claim 12, wherein said third shredding means comprises a rotary shear shredder, said third shredding means being in communication with said second shredding means and disposed below said predetermined fluid level of said separation tank means.

15. A process for the continuous treatment of infectious waste material, which comprises:
  (a) introducing bulk unseparated infectious waste material into a receiving container means, said receiving container means being in communication with a shredding means whereby bulk unseparated infectious waste material supplied to said receiving container means is conducted to said shredding means;
  (b) shredding said bulk unseparated waste material by said shredding means;
  (c) transferring the shredded waste material from said shredding means to a separation tank means having a fluid filling means to provide a predetermined fluid level in said separation tank means and removing from said shredded waste material any glass and metal components which settle by gravity in a lowermost portion of said separation tank means to form a waste slurry;
  (d) transferring said waste slurry from said separation tank means of step (c) to a second shredding means and reducing the size of particles in said waste slurry by said second shredding means;
  (e) transferring said waste slurry from said second shredding means to a disinfection vessel means, said disinfection vessel means comprising a first disinfection means communicating in series relationship with at least one second disinfection means, and contacting said waste slurry in said disinfection vessel means with a disinfectant comprising ozone in gas phase and in aqueous solution for a sufficient amount of time to disinfect said waste slurry by flowing said waste slurry through a disinfection tube positioned centrally in said disinfection vessel means in a direction opposite to the buoyancy of ozone gas bubbles in contact with said waste slurry and continuously monitoring the concentration of said ozone in said disinfection vessel means by an analyzing means communicating with said disinfection vessel means; and
  (f) transferring said disinfected waste slurry to a dewatering means to remove liquid therefrom and recover solid components of said disinfected waste slurry.

16. The process of claim 15, further including the step of transferring said waste slurry from said second shredding means of step (e) to a third shredding means to further reduce the size of particles in said waste slurry prior to transferring said waste slurry into said disinfection vessel means.

17. The process of claim 15, wherein said second shredding means is a rotary shear shredder, said second shredding means being in communication with said separation tank means and disposed below said predetermined fluid level of said separation tank means.

18. The process of claim 16, wherein said third shredding means is a rotary shear shredder, said third shredding means being in communication with said second shredding means and disposed below said predetermined fluid level of said separation tank means.

19. An apparatus for the continuous treatment of infectious waste material, which comprises:
  (a) receiving container means for receiving bulk unseparated infectious waste;
  (b) a shredding means in communication with said receiving container means for reducing the particle size of said bulk unseparated infectious waste material;
  (c) a separation tank means in communication with said shredding means for separating and removing glass and metal components which settle by gravity to a lowermost portion of said separation tank means, said separation tank means having a fluid filling means for providing a predetermined fluid level in said separation tank means and forming a waste slurry in said separation tank means;
  (d) a disinfection vessel means communicating with said separation tank means of item (c) for receiving and disinfecting said waste slurry, said disinfection vessel means comprising a first disinfection means communication in series relationship with at least one second disinfection means;
  (e) an ozone source means communicating with said disinfection vessel means for introducing ozone in gas phase and in aqueous solution to said disinfection vessel means for disinfecting said waste slurry; and
  (f) a dewatering means communicating with said disinfection vessel means to receive said disinfected waste slurry and to remove liquid therefrom and recover solid components of said disinfected waste slurry.

20. The apparatus of claim 19, further including a second shredding means communicating with said separation tank means of item (c) to reduce the size of particles in said waste slurry prior to transferring said waste slurry into said disinfection vessel means.

21. The apparatus of claim 20, further including a third shredding means communicating with said second shredding means to further reduce the size of particles in said waste slurry prior to transferring said waste slurry into said disinfection vessel means.

22. The apparatus of claim 20, wherein said second shredding means is a rotary shear shredding in communication with said separation tank means and disposed below said predetermined fluid level of said separation tank means.

23. The apparatus of claim 21, wherein said third shredding means is a rotary shear shredder in communication with said second shredding means and disposed below said predetermined fluid level of said separation tank means.

24. The apparatus of claim 19, further including an analyzing means communicating with said disinfection vessel means for continuously monitoring the concentration of ozone in said disinfection vessel means.

25. The apparatus of claim 19, wherein said second disinfection means comprises from 1 to about 10 disinfection tanks communicating in series relationship.

26. The apparatus of claim 19, wherein said separation tank means further includes a means for pulping paper components included in the bulk unseparated infectious waste material and transferring such pulped paper components to said disinfection vessel means.

27. The apparatus of claim 19, wherein said shredding means comprises a rotary shear shredder.

28. The apparatus of claim 19, wherein each of said first disinfection means and said second disinfection means further includes a centrally disposed infection tube communicating with said ozone source means.

* * * * *